United States Patent [19]

Mork et al.

[11] Patent Number: 5,977,194
[45] Date of Patent: Nov. 2, 1999

[54] HIGH INTERNAL PHASE EMUSIONS AND POROUS MATERIALS PREPARED THEREFROM

[75] Inventors: Steven W. Mork; Gene D. Rose, both of Midland, Mich.

[73] Assignee: The Dow Chemical Company, Midland, Mich.

[21] Appl. No.: 08/558,333

[22] Filed: Nov. 15, 1995

[51] Int. Cl.$^6$ .................................................. C08J 9/28
[52] U.S. Cl. .................. 521/61; 252/182.29; 252/304; 252/306; 252/307; 521/62; 521/63; 521/64; 521/114; 521/128; 521/129; 521/130; 521/140; 521/142; 521/146; 521/149; 521/150
[58] Field of Search .................. 521/61, 62, 63, 521/64, 114, 128, 129, 130, 140, 142, 146, 149, 150; 252/182.29, 304, 306, 307

[56] References Cited

U.S. PATENT DOCUMENTS

| | | |
|---|---|---|
| Re. 27,444 | 7/1972 | Will . |
| 3,244,772 | 4/1966 | Wolf von Bonin et al. . |
| 3,343,599 | 9/1967 | Eddins, Jr. et al. . |
| 3,352,109 | 11/1967 | Lissant .................................. 60/217 |
| 3,378,418 | 4/1968 | Lissant .................................. 149/109 |
| 3,396,537 | 8/1968 | Lissant et al. . |
| 3,423,826 | 1/1969 | Liska . |
| 3,490,237 | 1/1970 | Lissant . |
| 3,539,406 | 11/1970 | Lissant . |
| 3,613,372 | 10/1971 | Lissant . |
| 3,617,095 | 11/1971 | Lissant .................................. 302/66 |
| 3,734,867 | 5/1973 | Will . |
| 3,886,107 | 5/1975 | Najvar . |
| 3,892,881 | 7/1975 | Lissant . |
| 3,974,116 | 8/1976 | Lissant . |
| 3,983,213 | 9/1976 | Lissant . |
| 3,984,334 | 10/1976 | Hopper . |
| 3,988,508 | 10/1976 | Lissant .................................. 526/344 |
| 4,018,426 | 4/1977 | Mertz et al. .................................. 259/7 |

(List continued on next page.)

FOREIGN PATENT DOCUMENTS

| | | |
|---|---|---|
| 2145030 | 9/1996 | Canada . |
| 0 068 830 | 1/1983 | European Pat. Off. . |
| 0 130 764 | 1/1985 | European Pat. Off. . |
| 0 060 138 | 9/1986 | European Pat. Off. . |
| 0 297 179 | 1/1989 | European Pat. Off. . |
| 0 200 528 | 1/1996 | European Pat. Off. . |
| 1 458 203 | 12/1976 | United Kingdom . |
| 2 054 635 | 2/1981 | United Kingdom . |
| 2 131 430 | 6/1984 | United Kingdom . |
| 97/45456 | 12/1947 | WIPO . |
| WO 96/21474 | 7/1986 | WIPO . |
| WO 89/12618 | 12/1989 | WIPO . |
| WO 93/04092 | 3/1993 | WIPO . |
| WO 93/04113 | 3/1993 | WIPO . |
| WO 94/13704 | 6/1994 | WIPO . |
| WO 96/40823 | 12/1996 | WIPO . |
| WO 97/07832 | 3/1997 | WIPO . |
| WO 97/18246 | 5/1997 | WIPO . |
| WO 97/19129 | 5/1997 | WIPO . |
| 97/37745 | 10/1997 | WIPO . |
| 97/45479 | 12/1997 | WIPO . |

OTHER PUBLICATIONS

Williams et al., "Emulsion Stability and Rigid Foams from Styrene or Divinylbenzene Water–in–Oil Emulsions" *Langmuir*, vol. 6, pp. 437–444 (1990).

Williams et al., "Spatial Distribution of the Phases in Water–in–Oil Emulsions. Open and Closed Microcellular Foams from Crosslinked Polystyrene," *Langmuir*, vol. 4, pp. 656–662 (1988).

Yerges, "Sound, Noise, and Vibration Control," 2nd Ed., Van Nostrand REinhold Co., p. 59 (1978).

Reichle, Walter T., "Cataltic Reactions by Thermally Activated, Synthetic, Anionic Caly Minerals", *Journal of Catalysis*, vol. 94, pp. 547–557 (1985).

Lissant, "Making and Breaking Emulsions", Emulsion and Emulsion Technology Part 1, Chpt. 2, pp. 71–124 (1974).

Lewis, Hawley's Condensed Chemical Dictionary, $12^{th}$ Ed., p. 43 (1993).

Gmitter et al., "Flexible Polyurethane Foams", Palstic Foams, Part III, pp. 109–226 (1972).

Derwent Publications Ltd. JP 61 231 098 A, Kao Corporation.

Yokota et al. "Synthesis of Polymerizable Surfactant and its Application to Emulsion Polymerization", Industrial Applications of Surfactants III, pp. 31–48 (1992).

Nagai, Katsutoshi, "Radical Polymerization and Potential Applications of Surface–active Monomers", *TRIP*, vol. 4, #4, Apr. 1996.

"High Internal Phase Emulsions (HIPEs) and Foams Made Therefrom", filed in the United States of America on Nov. 18, 1998, Application Serial No. 09/195,273; Applicants: Steven W. Mork et al.

"Multilayer Porous Polymeric Material and Process For Preparing Teh Same", filed in the United States of America on Aug. 10, 1998, Application serial. No. 09/131,307; Applicant: Steven W. Mork.

"High Internal Phase Emulsions and Porous Materials Prepared Therefrom", filed at the PCT on Apr. 17, 1998, International Application No. US/PCT98/07586, Applicant: Steven W. Mork et al.

"Method For Treating Subterranean Formations", filed in the United States of America on Oct. 12, 1998, Application Serial No. 60/104,169; Applicant: Gene R. Rose et al.

"High Interanl Phase Emulsions and Porous Materials Prepared Therefrom", filed in the United States of America on Jun. 16, 1998, Application Serial No. 09/98,259; Applicants: Steven W. Mork et al.

*Primary Examiner*—John M. Cooney, Jr.
*Attorney, Agent, or Firm*—Nemia C. Damocles

[57] ABSTRACT

High internal phase emulsions having an internal aqueous phase of greater than 70 percent by volume and an external oil phase comprising a vinyl polymerizable monomer contain a surfactant capable of chemically binding to the polymerizable monomer. Polymeric foams having a high internal phase emulsion stabilizing surfactant chemically bound to the polymeric material and a liquid capacity of from about 70 to 99 percent of its saturated volume can be prepared from such emulsions.

37 Claims, No Drawings

U.S. PATENT DOCUMENTS

| | | | |
|---|---|---|---|
| 4,037,665 | 7/1977 | Hopper . | |
| 4,168,239 | 9/1979 | Mertz et al. | 252/2 |
| 4,259,215 | 3/1981 | Murata et al. | 252/528 |
| 4,473,611 | 9/1984 | Haq | 428/198 |
| 4,522,953 | 6/1985 | Barby et al. | 521/64 |
| 4,536,521 | 8/1985 | Haq | 521/146 |
| 4,538,000 | 8/1985 | Parr | 568/616 |
| 4,603,069 | 7/1986 | Haq et al. | 428/76 |
| 4,606,913 | 8/1986 | Aronson et al. | 424/59 |
| 4,606,958 | 8/1986 | Haq et al. | 428/68 |
| 4,608,197 | 8/1986 | Kesling, Jr. et al. | 252/551 |
| 4,611,014 | 9/1986 | Jomes etal. | 521/146 |
| 4,612,334 | 9/1986 | Jones et al. | 521/146 |
| 4,659,564 | 4/1987 | Cox et al. | 424/65 |
| 4,668,709 | 5/1987 | Jones et al. | 521/146 |
| 4,745,154 | 5/1988 | Ruffner | 524/801 |
| 4,746,460 | 5/1988 | Taylor | 252/314 |
| 4,775,655 | 10/1988 | Edwards et al. | 502/416 |
| 4,788,225 | 11/1988 | Edwards et al. | 521/147 |
| 4,797,310 | 1/1989 | Barby et al. | 428/71 |
| 4,889,885 | 12/1989 | Usuki et al. | 524/445 |
| 4,965,100 | 10/1990 | Leigh et al. | 427/242 |
| 4,965,289 | 10/1990 | Sherrington et al. | 521/53 |
| 4,985,468 | 1/1991 | Elmes et al. | 521/63 |
| 5,006,339 | 4/1991 | Bargery et al. | 424/404 |
| 5,021,462 | 6/1991 | Elmes et al. | 521/63 |
| 5,147,345 | 9/1992 | Young et al. | 604/378 |
| 5,149,720 | 9/1992 | DesMarais et al. | 521/63 |
| 5,150,576 | 9/1992 | Minzenberger | 62/11 |
| 5,162,475 | 11/1992 | Tang et al. | 526/333 |
| 5,187,070 | 2/1993 | Fung et al. | 435/25 |
| 5,198,472 | 3/1993 | DesMarais et al. | 521/63 |
| 5,200,433 | 4/1993 | Beshouri | 521/64 |
| 5,210,104 | 5/1993 | Bass et al. | 521/64 |
| 5,250,576 | 10/1993 | DesMarais et al. | 521/63 |
| 5,252,619 | 10/1993 | Brownscombe et al. | 521/64 |
| 5,260,345 | 11/1993 | DesMarais et al. | 521/148 |
| 5,268,224 | 12/1993 | DesMarais et al. | 428/286 |
| 5,290,820 | 3/1994 | Brownscombe et al. | 521/64 |
| 5,292,777 | 3/1994 | Desmarais et al. | 521/64 |
| 5,296,627 | 3/1994 | Tang et al. | 558/33 |
| 5,306,734 | 4/1994 | Bass et al. | 521/63 |
| 5,318,554 | 6/1994 | Young et al. | 604/378 |
| 5,324,862 | 6/1994 | Yokota et al. | 568/608 |
| 5,331,015 | 7/1994 | DeMarais et al. | 521/64 |
| 5,332,854 | 7/1994 | Yokota et al. | 558/33 |
| 5,334,621 | 8/1994 | Beshouri | 521/64 |
| 5,348,974 | 9/1994 | Wright et al. | 514/456 |
| 5,352,711 | 10/1994 | DesMarais | 521/149 |
| 5,358,974 | 10/1994 | Brownscombe et al. | 521/64 |
| 5,387,207 | 2/1995 | Dyer et al. | 604/369 |
| 5,397,316 | 3/1995 | LaVon et al. | 604/369 |
| 5,500,451 | 3/1996 | Goldman et al. | 521/64 |
| 5,550,167 | 8/1996 | DesMarais | 521/50 |
| 5,563,179 | 10/1996 | Stone et al. | 521/64 |
| 5,571,849 | 11/1996 | DesMarais | 521/64 |
| 5,632,737 | 5/1997 | Stone et al. | 604/358 |
| 5,633,291 | 5/1997 | Dyer et al. | 521/64 |
| 5,641,433 | 6/1997 | Chirinos et al. | 252/312 |
| 5,646,193 | 7/1997 | Brownscombe et al. | 521/63 |
| 5,649,920 | 7/1997 | Levon et al. | 604/385.2 |
| 5,650,222 | 7/1997 | DesMarais et al. | 442/370 |
| 5,652,194 | 7/1997 | Dyer et al. | 502/402 |
| 5,670,087 | 9/1997 | Chirinos et al. | 252/311.5 |
| 5,692,939 | 12/1997 | DesMarais et al. | 442/373 |
| 5,728,743 | 3/1998 | Dyer et al. | 521/64 |
| 5,741,581 | 4/1998 | DesMarais et al. | 428/284 |
| 5,744,506 | 4/1998 | Goldman et al. | 521/64 |
| 5,753,359 | 5/1998 | Dyer et al. | 428/315.5 |
| 5,763,499 | 6/1998 | DesMarais et al. | 521/64 |
| 5,767,168 | 6/1998 | Dyer et al. | 521/149 |
| 5,770,634 | 6/1998 | Dyer et al. | 521/64 |
| 5,786,395 | 7/1998 | Stone et al. | 521/64 |
| 5,795,921 | 8/1998 | Dyer et al. | 521/146 |
| 5,817,704 | 10/1998 | Shiveley et al. | 521/63 |
| 5,851,430 | 12/1998 | Chirinos et al. | 252/311.5 |
| 5,856,366 | 1/1999 | Shiveley et al. | 521/63 |

HIGH INTERNAL PHASE EMUSIONS AND POROUS MATERIALS PREPARED THEREFROM

BACKGROUND OF THE INVENTION

This invention relates to water-in-oil high internal phase emulsions and the porous polymeric materials produced therefrom.

Water-in-oil emulsions are dispersions of discontinuous or discrete water particles commonly referred to as the "internal" aqueous phase in a continuous or "external" oil phase. Emulsions can contain as much and more than 70 volume percent internal phase. These are often referred to as high internal phase emulsions (HIPEs). The volume fraction of the internal aqueous phase in such emulsions can be as high as 90 percent and frequently is as high as 95 percent with some HIPEs being reported as high as 98 percent aqueous phase.

The use of high internal phase emulsions (HIPEs) in forming porous polymeric materials are well known and are described, for example, in Shell Oil Company (Shell) U.S. Pat. Nos. 5,210,104 and 5,200,433; Lever Brothers Company (Lever) U.S. Pat. Nos. 4,536,521 and 4,788,225; and The Procter & Gamble Company (P & G) U.S. Pat. Nos. 5,147,345; 5,331,015; 5,260,345; 5,268,224 and 5,318,554. In the described HIPEs, the external oil phase typically comprises a vinyl polymerizable monomer, such as 2-ethylhexyl acrylate and styrene, and a cross-linking monomer such as divinylbenzene. The internal aqueous phase typically comprises water, a radical initiator (if not in the oil phase) and an electrolyte. To form a stable emulsion, a surfactant is added to the oil phase prior to emulsification. Commonly used emulsion stabilizing surfactants include, for example, nonionic surfactants, such as sorbitan esters (e.g., sorbitan monooleate and sorbitan monolaurate). The resulting emulsion is then subjected to polymerization conditions which are sufficient to polymerize the monomers in the oil phase to form a porous polymer.

HIPE polymerization has gained increasing interest, since polymeric foams having the capacity to absorb relatively high amounts of water and other liquids can be produced. Unfortunately, in many applications, e.g., as absorbents, the emulsion stabilizing surfactant should be removed from the porous polymeric foam prior to use. For example, as described in U.S. Pat. No. 5,331,015, the surfactant may be an extractable residue which can be removed through post-polymerization rinses. If not removed, the surfactant residue may create a problem when it comes in contact with sensitive human skin.

However, upon removal of the emulsion stabilizing surfactant, the foam generally becomes less hydrophilic. It must then be further treated to render it sufficiently hydrophilic for use as an aqueous fluid absorbent. One suggested method for rendering the foam more hydrophilic involves chemically modifying (i.e., sulfonating or esterifying) the polymeric foam; see, for example, U.S. Pat. No. 4,536,521. In another method, a hydrophilizing component (i.e., salt and/or a residual emulsifier) can be added to the foam; see, for example, U.S. Pat. No. 5,260,345. However, these techniques involve additional costs and/or are often of limited utility.

It would be desirable to provide a water-in-oil HIPE which, when polymerized, would produce a HIPE foam which does not contain a residual surfactant and which does not require a post-polymerization treatment to render it sufficiently hydrophilic to be useful as an absorbent for hydrophilic liquids.

SUMMARY OF THE INVENTION

In a first aspect, this invention is a water-in-oil high internal phase emulsion having an internal aqueous phase of greater than 70 percent by volume and an external oil phase comprising a vinyl polymerizable monomer and an emulsion stabilizing surfactant capable of chemically binding to the monomers that are being polymerized.

When polymerized, the emulsion stabilizing surfactant will react with the monomer(s) used in preparing HIPE foams or resulting polymer, thereby losing its surfactant characteristics while, at the same time, imparting hydrophilic properties to the resulting polymer. Surprisingly, these surfactants can render the emulsion stable, permit polymerization and yet render the HIPE products hydrophilic. The hydrophilicity of the resulting product varies and can be modified depending on the surfactant selected.

In a second aspect, this invention is such a process for preparing a porous polymeric material which comprises polymerizing the water-in-oil high internal phase emulsion comprising the surfactant capable of chemically binding to the monomers that are polymerized. In a third aspect, this invention is an open-cell porous polymeric material having a high internal phase emulsion stabilizing surfactant chemically bound to the polymeric material and a liquid capacity of from about 70 to about 99 percent of its saturated state volume. The foams prepared from HIPEs containing these reactive, emulsion stabilizing surfactants will contain relatively small amounts of extractable surfactants. The term "relatively small amounts of extractable surfactants" means that less than 50 percent by weight, preferably less than 25 percent by weight and most preferably less than 10 percent by weight of the surfactant can be extracted from the foam using simple rinses with water or typical solvents for the surfactants, such as, for example, methanol or isopropanol.

The HIPEs of the present invention are useful in preparing highly absorbent polymeric foam materials with a range of hydrophilicity, depending on the nature and concentration of the chemically bound surfactant. Adjusting the range of hydrophilicity of the polymeric foam materials allows absorption of fluids ranging from non-polar hydrocarbons to aqueous solutions. Highly hydrophilic foam materials made according to the present invention have a particularly useful application in the manufacture of diapers, or other articles which absorb or retain aqueous body fluids.

DETAILED DESCRIPTION OF THE INVENTION

The high internal phase emulsion (HIPE) of the present invention is a water-in-oil emulsion having an internal aqueous phase greater than about 70 percent by volume, preferably greater than about 90 percent by volume, and most preferably greater than about 95 percent by volume, and an external oil phase. HIPEs of as much as 98 volume percent or more of internal aqueous phase can be made by the present invention. The external oil phase comprises one or more vinyl polymerizable monomers and a cross-linking monomer. The internal aqueous phase comprises water. Typically, a water-soluble radical initiator is added in the aqueous phase. If an oil-soluble initiator is employed, it is added in the oil phase. Additionally, the HIPE comprises a surfactant capable of chemically binding to the monomers that are polymerized or the resulting polymers.

Vinyl polymerizable monomers which can be employed in the practice of the present invention are any polymerizable monomer having an ethylenic unsaturation. In general, the HIPEs are advantageously prepared from either or both (i) at least one monomer that tends to impart glass-like properties (glassy monomers) to the resulting porous polymeric material and (ii) at least one monomer that tends to impart rubber-like properties (rubbery monomers) to the resulting porous polymeric materials.

The glassy monomers are, for the purposes of the present invention, defined as monomeric materials which would produce homopolymers having a glass transition temperature above about 40° C. Preferred glassy monomers include methacrylate-based monomers, such as, for example, methyl methacrylate, and styrene-based monomers, such as, for example, various monovinylidene aromatics such as styrene, o-methylstyrene, chloromethylstyrene, vinylethylbenzene and vinyl toluene. More preferred glassy monomers include styrene, o-methylstyrene, and chloromethylstyrene. The most preferred glassy monomer is styrene.

The rubbery monomers are, for the purposes of the present invention, defined as monomeric materials which would produce homopolymers having a glass transition temperature of about 40° C. or lower. Preferred rubbery monomers include alkyl esters of ethylenically unsaturated acids ("acrylate esters" or "methacrylate" esters), such as 2-ethylhexyl acrylate, butyl acrylate, hexyl acrylate, butyl methacrylate, lauryl methacrylate, isodecyl methacrylate and mixtures thereof; vinyl aliphatic and alicyclic hydrocarbons such as butadiene; isoprene; and combinations of these comonomers. More preferred rubbery monomers include butyl acrylate, 2-ethylhexyl acrylate, butadiene, isoprene and combinations of these comonomers. The most preferred rubbery monomer is 2-ethylhexyl acrylate.

Preferably, the HIPE emulsion includes at least one glassy monomer and at least one rubbery monomer. Without being bound by theory, it is believed that the rubbery monomer provides the foams with flexibility and is used in an amount sufficient to allow compression, bending and twisting during processing, packaging, shipping, storing and use of absorbent articles containing such foams, as well as to allow the foam to remain thin until it absorbs liquid, if desired. It is believed the glassy monomer provides the foams with structural integrity and is used in an amount sufficient to minimize the incidence of foam tearing or fragmenting encountered when such foams are subjected to both dynamic and static forces such as, for example, when the wearer of a diaper containing the foam walks, runs, crawls or jumps. The ratio of the glassy monomer to the rubbery monomer generally ranges from about 1:25 to 1.5:1, more preferably from about 1:9 to 1.5:1.

While the amount of the vinyl polymerizable monomers most advantageously employed depends on a variety of factors, such as the specific monomers, in general, the vinyl polymerizable monomer is used in an amount of from about 70 to about 98 weight percent, preferably from about 80 to about 95 weight percent, and most preferably from about 85 to 93 weight percent, based on the total oil phase.

Cross-linking monomers which can be employed in the practice of the present invention for preparing the HIPE include any multifunctional unsaturated monomers capable of reacting with the vinyl monomers. Multifunctional unsaturated cross-linking monomers include, for example, divinylbenzene, ethylene glycol dimethacrylate, 3-butylene dimethacrylate, trimethylolpropane triacrylate and allyl methacrylate. While the amount of cross-linking monomers most advantageously employed depends on a variety of factors, such as the specific monomers, in general, the cross-linking monomer is used in an amount of from about 2 to about 50 weight percent, preferably from about 2 to about 20 weight percent, and most preferably from about 5 to about 15 weight percent, based on the total oil phase.

Radical initiators which can be employed in the practice of the present invention for preparing the HIPE include the water-soluble initiators such as, for example, potassium or sodium persulfate and various redox systems such as ammonium persulfate together with sodium metabisulfite and oil-soluble initiators, such as, for example, azobisisobutyronitrile (AIBN), benzoyl peroxide, methyl ethyl ketone peroxide and di-2-ethyl-hexyl-peroxydicarbonate and lauroyl peroxide. The initiator can be added to the aqueous phase or to the oil phase, depending on whether the initiator is water-soluble or oil-soluble. The initiator should be present in an effective amount to polymerize the monomers. Typically, the initiator can be present in an amount of from about 0.005 to about 20 weight percent, preferably from about 0.1 to about 10 weight percent and most preferably from about 0.1 to about 5 weight percent, based on the total oil phase.

The internal aqueous phase can include a water-soluble electrolyte for aiding the surfactant in forming a stable emulsion, controlling porosity of the foam and/or enhancing the hydrophilicity of the resulting polymeric foam material if left as a residual component of the foam material. Water-soluble electrolytes which can be employed in the practice of the present invention include inorganic salts (monovalent, divalent, trivalent or mixtures thereof), for example, alkali metal salts, alkaline earth metal salts and heavy metal salts such as halides, sulfates, carbonates, phosphates and mixtures thereof. Such electrolytes include, for example, sodium chloride, sodium sulfate, potassium chloride, potassium sulfate, lithium chloride, magnesium chloride, calcium chloride, magnesium sulfate, aluminum chloride and mixtures thereof. Mono- or divalent salts with monovalent anions, such as halides, are preferred. While the amount of electrolytes most advantageously employed depends on a variety of factors, such as the specific compound, the desired porosity of the foam and the surfactant employed, in general, the electrolytes can be employed up to about 10, more preferably up to about 5 and most preferably up to about 1 weight percent, based on the total aqueous mixture.

The internal aqueous phase can additionally comprise a non-electrolyte hydrophilizing component, such as, for example, glycerin, which can be left in the foam to enhance hydrophilicity as long as an HIPE can still be prepared and polymerized into a foam.

Surfactants which can be employed in the practice of the present invention include surfactants capable of chemically binding to the monomer(s) and/or the resulting polymer(s) at the conditions of polymerization. Such surfactants include surfactants having polymerizable vinyl groups and surfactants capable of undergoing a graft reaction (graftable surfactants) at the conditions of polymerization.

Surfactants having polymerizable vinyl groups which can be employed in the practice of the present invention include any substituted and/or conjugated alkene with hydrophilic and hydrophobic moieties which render the surfactant capable of forming the desired high internal phase water-in-oil emulsion. Preferred surfactants having polymerizable vinyl groups include quaternary ammonium compounds containing an alkyl group having more than 12 carbons, such as N,N-dimethyl, N-erucyl, N-vinylbenzyl ammonium chloride and oleyl-hydroxyethyl-vinylbenzyl imidazolinium chloride; and nonionic compounds such as acrylate- or methacrylate-capped poly(ethylene oxide) (EO)/polybutylene oxide (BO) diblock polymers and BO/EO/BO triblock polymers.

Generally, the quaternary ammonium compounds can be prepared by combining an appropriate alkyl chloride and a tertiary amine according to well-known chemistry. Preparations of the aforementioned quaternary ammonium compounds are described in detail in the examples.

In general, capped nonionic polymers can be prepared using well-known chemistry, by reacting the appropriate acid chloride with an alcohol-terminated block polymer, for example, by reacting acryloyl chloride with an EO/BO diblock polymer terminated with an alcohol on the BO end. Block lengths of the EO and BO units can vary. Those skilled in the art will be able to balance the absolute and relative lengths of the units in order to create a surfactant capable of forming an appropriate HIPE.

Preferred surfactants capable of undergoing a graft reaction (graftable surfactants) include compounds which form radicals upon abstraction of a portion of the compound (a hydrogen radical abstraction, for example). Abstraction methods are well known in the art of polymerization and grafting. See, for example, R. J. Ceresa, "Free-Radical Grafting By Transfer Mechanisms", *Soc. Chem. Ind.*, Monograph No. 20, 249–257, discussion 257–260 (1966). Preferred graftable surfactants can either be non-polymeric or polymeric.

Graftable non-polymeric surfactants which can be employed in the practice of the present invention include any compound with hydrophilic and hydrophobic moieties that render it capable of forming the desired water-in-oil HIPE and that contains an element or group which can be extracted to form a radical. For example, hydrogen radicals are readily extracted from compounds containing benzylic or allylic hydrogens and ethers with α-hydrogens. Examples of graftable non-polymeric surfactants are benzylamines. Benzylamines can be synthesized according to well-established reactions with benzylchloride and alkyl amines. In general, benzylamines capable of stabilizing the HIPE can be obtained by varying the alkyl lengths of the amine.

Graftable polymeric surfactants which can be employed in the practice of the present invention include surfactants containing poly(ethylene oxide), poly(butylene oxide) and/or benzyl functionalities.

The amount of surfactant used must be such that a water-in-oil high internal phase emulsion will form. Generally, the surfactant can be present in an amount of from about 2 to about 40 percent by weight, preferably from about 5 to about 25 percent by weight and most preferably from about 10 to about 25 percent by weight, based on the oil phase.

Methods for preparing water-in-oil emulsions are known in the art such as, for example, in U.S. Pat. Nos. 4,522,953 and 5,210,104, both of which are incorporated herein by reference, and these methods can be employed in the practice of the present invention. For example, the water-in-oil HIPE can be prepared in batches. In general, to form a water-in-oil HIPE in batch quantities, the water phase is gradually added to a mixture of oil phase and surfactant while the mixture is being agitated. Agitation can be accomplished any number of ways including impeller-type agitation. Alternatively, water-in-oil HIPEs can be prepared in a continuous flow manner. Methods for continuous flow HIPE preparation are also well established in the literature. See, for example, U.S. Pat. Nos. 4,018,426 and 5,198,472, both of which are incorporated herein by reference.

Polymerization conditions can vary depending on the initiator system used and the properties of the polymer desired. Polymerization using potassium persulfate and/or lauroyl peroxide are typically done at about 60° C. for about 18 hours. However, polymerizations can be carried out at other temperatures as long as the HIPE remains stable and the initiator system is effective at that temperature. Generally, increased temperatures decrease the required polymerization time. Faster polymerizations generally produce shorter polymer chains which may change the physical properties of the resulting foam.

The following working examples are given to illustrate the invention and should not be construed to limit its scope. Unless otherwise indicated, all parts and percentages are by weight.

EXAMPLE 1

A polymerizable quaternary ammonium surfactant is prepared by combining 5.7 g of vinylbenzyl chloride and 13.1 g of dimethylerucylamine in a glass jar. A freshly scraped copper wire is added to reduce the probability of polymerization. The jar is capped and placed on a mechanical shaker at low speed for approximately 40 hours. The solution goes from a straw-colored non-viscous liquid to a light-yellow, waxy, plastic-like solid.

The reaction is characterized using $^1$H NMR. The reaction product, N,N-dimethyl, N-erucyl, N-vinylbenzyl ammonium chloride, is dissolved in $DCCl_3$ containing 1 percent TMS by weight, and spectra are collected on a Varian Gemini-300 NMR. Percent conversion is determined relative to both vinylbenzyl chloride (VBC) and dimethylerucylamine (DMEA) reactants. Benzylic protons on VBC appear at 4.6 ppm (all the peak positions are given relative to TMS) while the quaternary ammonium surfactant benzylic protons appear at 5.1 ppm. The ratio of integrated benzylic proton peak areas for the quaternary ammonium surfactant relative to VBC is 52.7, corresponding to better than 98 percent molar conversion of the VBC. The N,N-dimethyl protons of the amine appear at 2.2 to 2.4 ppm while in the quaternary ammonium surfactant they appear at 3.2 to 3.4 ppm. The ratio of integrated N,N-dimethyl proton peak areas for the quaternary ammonium surfactant relative to DMEA is 57.3, again corresponding to better than 98 percent molar conversion of the amine.

A solution of organic monomers and surfactant is prepared by dissolving 1.5 g of the quaternary ammonium chloride into 3.62 g of styrene. To this solution is added 5.32 g 2-ethylhexyl acrylate and 0.91 g of 55 percent active divinylbenzene. An aqueous phase is prepared by dissolving 1.65 g calcium chloride dihydrate and 0.38 g potassium persulfate into 148 g of deionized water. The HIPE is prepared in an 8-ounce glass jar by dropwise adding the aqueous phase to the organic monomers and surfactant solution while agitating at 500 rpm with a Cowles-type agitator. The jar is periodically repositioned or moved up and down to avoid puddling of the aqueous phase. Once all of the aqueous phase has been added, the emulsion is mixed an additional 2 minutes to ensure homogeneous mixing. The resulting emulsion is white and has the consistency of mayonnaise. Portions of the emulsion are poured into Pyrex® (Corning Glass) dishes (~50 mm in diameter), covered with SARAN WRAP® (The Dow Chemical Company) and cured in a forced air oven at 60° C. for 18 hours.

The cured samples are white porous polymeric materials approximately 50 mm in diameter and 10 mm thick, saturated in the aqueous phase. Samples are squeezed to remove most of the aqueous phase. Each sample is rinsed three times in fresh deionized water, and rinsed three times in fresh isopropanol. Each rinse consists of at least three compression cycles where the polymeric material is fully compressed while submerged and then allowed to re-swell. Samples are squeezed between paper towels after each rinse. After the last isopropanol rinse, the materials are allowed to air dry and then analyzed for nitrogen.

Pyrolysis gas chromatography (GC) with an atomic emission detector (AED) is used to analyze the material for bound quaternary ammonium surfactant. Detection is done at 174 nm, corresponding to a nitrogen emission. First, a blank foam, made with the above recipe except using sorbitan monooleate (Span® 80, ICI Americas Co.) instead of the quaternary ammonium surfactant, is analyzed to establish a background chromatogram. Then a sample of the quaternary ammonium surfactant is analyzed to determine distinguishing peaks. The surfactant has a unique doublet of peaks between 12- and 13-minute retention times. The polymeric foam material made from the quaternary ammonium surfactant-containing HIPE also has a doublet of peaks between 12 and 13 minutes, confirming the presence of the quaternary ammonium compound.

To ensure that the quaternary ammonium compound is not an unbound residual surfactant, the foam is rinsed thoroughly in 10 mL of methanol. Methanol proves to be a slightly better solvent for the surfactant than isopropanol. All of the methanol is collected, concentrated down to 0.5 mL and then analyzed by pyrolysis GC to see if it contains any extractable emulsifier. No quaternary ammonium surfactant could be detected in the methanol rinse, confirming that greater than 95 percent of the previously observed quaternary ammonium surfactant remains in the material after the methanol rinse.

By combustion chemiluminescence, it is determined that approximately 94 percent of the quaternary ammonium surfactant used in the HIPE remains bound to the foam.

EXAMPLE 2

A second quaternary ammonium surfactant is prepared as described in Example 1, using 6.1 g VBC and 14.6 g oleyl-hydroxyethyl-imidazoline (Miramine OC, Rhone-Poulenc). The solution goes from a non-viscous, yellow solution to a light-amber, very elastic material.

The extent of conversion is determined by $^1$H NMR by comparing benzyl proton transitions. The VBC benzyl protons appear at 4.6 ppm, relative to TMS, while the quaternary ammonium surfactant benzyl protons appear at 4.7 ppm. The ratio of integrated benzyl proton peaks for the quaternary ammonium surfactant to VBC is 7.25, corresponding to approximately 88 mole percent conversion.

An HIPE is prepared and polymerized as described in Example 1, substituting oleyl-hydroxyethyl-vinylbenzyl imidazolinium chloride for N,N-dimethyl, N-erucyl, N-vinylbenzyl ammonium chloride.

The material could be squeezed slowly between paper towels to remove most of the aqueous phase. Three rinses in deionized water and isopropanol are done as described in Example 1. The foam is allowed to air dry after the last isopropanol rinse. Unlike the material in Example 1, this second material shrinks upon drying, resulting in a thin, flexible foam.

Analysis is done by pyrolysis GC as described in Example 1. Unique peaks corresponding to the Miramine quaternary ammonium emulsifier surfactant appeared at 5-, 6.2-, and 7.5-minute retention times, with the peak at 5 minutes having the largest area. The HIPE foam made with the quaternary ammonium surfactant reveals a peak at 5 minutes, confirming the presence of the quaternary ammonium compound. The sample is then rinsed thoroughly in 10 mL of methanol, which is collected, concentrated to 0.5 mL, and analyzed by pyrolysis GC. A very minor peak appears in the chromatogram of the methanol. Nonetheless, it is estimated that greater than 95 percent of the originally detected quaternary ammonium surfactant remains bound in the foam material.

Combustion chemiluminescence confirms that approximately 80 percent of the quaternary ammonium surfactant used in the HIPE remains bound in the foam.

EXAMPLE 3

A polymerizable, nonionic, polymeric surfactant is prepared by capping a poly(butylene oxide)/poly(ethylene oxide)/poly(butylene oxide) triblock polymer with methacrylate functionalities. The BO/EO/BO polymer is prepared by standard polymerization techniques, first growing the poly(EO) with two live radical ends, and then growing the poly(BO) on either end. The resulting polymer has a total molecular weight of 5658 and a poly(EO) molecular weight of 1338. The triblock polymer is capped using methacroyl chloride to provide the methacrylate functionalities on both poly(BO) ends.

A solution is prepared by dissolving 1.12 g of the above polymeric surfactant into a mixture of 2.42 g 2-ethylhexyl acrylate, 1.62 g styrene, and 0.51 g divinylbenzene (55 percent active). Into this solution is dissolved 0.11 g lauroyl peroxide. The mixture is mixed at 500 rpm with a high-speed disk impeller blade (Cowle's-type agitator) and 78.12 g of deionized water is added dropwise. A creamy-white water-in-oil HIPE is obtained.

The HIPE is poured into PYREX® dishes, covered with SARAN WRAP® and polymerized in a forced air oven at 65° C. for 16 hours. The polymerized material is white and porous with a slight bit of "scum" on the surface. The scum is removed and the water-saturated foam is squeezed dry between towels. The foam is rinsed three times in methanol to remove any unbound organic components, three times in deionized water, compressed to remove most of the remaining water, and dried to approximately 18 weight percent residual water. Rinses are done to remove any unbound components so they would not affect the absorbency or NMR analysis of the foam. The foam remains thin (approximately 20 percent of its saturated thickness). High resolution NMR analysis indicates the presence of poly(EO) and poly(BO) in the rinsed foam, confirming that surfactant has become bound.

The dried foam is set in a dish of deionized water and re-expanded as it absorbed the water. After 5 minutes, the foam has increased to nearly seven times its dry weight.

EXAMPLE 4

A solution is prepared by dissolving 0.3 g of the polymeric surfactant described in Example 3 into a mixture of 1.44 g 2-ethylhexyl acrylate, 0.93 g styrene, and 0.29 g divinylbenzene (55 percent active). Into this solution is dissolved 0.07 g dilauroyl peroxide. The mixture is mixed at 500 rpm with a high-speed disk impeller blade (Cowle's-type agitator) and 77 g of deionized water is added dropwise. A creamy-white water-in-oil HIPE is obtained.

The HIPE is poured into PYREX® dishes, covered with SARAN WRAP® and polymerized in a forced air oven at 65° C. for 17 hours. The polymerized material is white and porous with a slight bit of standing water on the surface. The water-saturated foam is rinsed three times in methanol to remove any unbound organic components, three times in deionized water, and three times in methylene chloride to ensure no unbound organic components remained. Any unbound components are removed so as to not affect the absorbency or NMR analysis of the foam. A portion of the foam is analyzed by high resolution NMR which revealed nearly all, if not all, of the BO/EO/BO compound remained bound into the foam.

After NMR analysis, the remaining foam is rinsed in methanol and then water, compressed to remove most of the water and oven dried to approximately 11 weight percent water. The foam remains in a collapsed state. This sample is set in a deionized water bath at room temperature and allowed to rehydrate. The sample re-expands as it absorbs water, increasing in weight over ten-fold within 60 minutes.

EXAMPLE 5

A polymerizable, nonionic, polymeric diblock surfactant is prepared by block polymerizing ethylene oxide (EO) and then butylene oxide (BO). The BO block is then capped using acryloyl chloride. The diblock polymer consists of approximately 750 molecular weight poly(EO) and approximately 1750 molecular weight poly(BO).

A solution is prepared by dissolving 0.56 of the above-described EO/BO diblock polymer into a mixture of 1.25 g 2-ethylhexyl acrylate, 0.52 g styrene, and 0.41 g divinylbenzene (55 percent active). Into this solution is dissolved 0.06 g lauroyl peroxide. The mixture is mixed at 500 rpm with a high-speed disk impeller (Cowle's-type agitator) while an aqueous solution consisting of 0.70 g of calcium chloride dihydrate dissolved in 76.43 g of deionized water is added dropwise. A very thick, white water-in-oil HIPE is obtained.

The HIPE is placed into PYREX® dishes, covered with SARAN WRAP® and polymerized in a forced air oven at 65° C. for 16 hours. The polymerized material is white and porous with a slight bit of "scum" and standing water on the surface. The scum is removed and the water-saturated foam is squeezed dry between towels. The foam is rinsed thoroughly in methanol and in deionized water in order to remove any residual salt or unbound surfactant. Unbound components are removed so as not to affect the absorbency or NMR analysis of the foam.

The rinsed foam is squeezed between paper towels and oven dried to approximately 22 weight percent water. The sample absorbs over 16 grams of water per gram of "dry" foam (g/g uptake). A portion of the foam is analyzed by high resolution $C^{13}$ NMR. The NMR analysis is consistent with approximately 50 percent of the surfactant remaining bound into the foam.

Additional samples prepared in a similar manner demonstrate greater than 20 g/g uptake of water.

What is claimed is:

1. A water-in-oil high internal phase emulsion having an internal aqueous phase of greater than 70 percent by volume and an external oil phase comprising a vinyl polymerizable monomer and a high internal phase emulsion stabilizing surfactant of which at least 50 weight percent chemically binds to the monomers that are polymerized.

2. The emulsion of claim 1, wherein the surfactant is a surfactant having polymerizable vinyl groups.

3. The emulsion of claim 2, wherein the surfactant having polymerizable vinyl groups is a substituted and/or conjugated alkene having hydrophilic and hydrophobic moieties which render the surfactant capable of forming a water-in-oil emulsion.

4. The emulsion of claim 2, wherein the surfactant having polymerizable vinyl groups is a quaternary ammonium compound.

5. The emulsion of claim 4, wherein the quaternary ammonium compound is N,N-dimethyl, N-erucyl, N-vinylbenzyl ammonium chloride or oleyl-hydroxyethyl-vinylbenzyl imidazolinium chloride.

6. The emulsion of claim 2, wherein the vinyl polymerizable monomer is a glassy monomer, a rubbery monomer or mixtures thereof.

7. The emulsion of claim 6, wherein the glassy monomer is a methacrylate-based monomer or a styrene-based monomer.

8. The emulsion of claim 7, wherein the methacrylate-based monomer is methyl methacrylate and the styrene-based monomer is styrene.

9. The emulsion of claim 6, wherein the rubbery monomer is 2-ethylhexyl acrylate, butyl acrylate, hexyl acrylate, butyl methacrylate, lauryl methacrylate, isodecyl methacrylate, butadiene or isoprene.

10. The emulsion of claim 9, wherein the rubbery monomer is 2-ethylhexyl acrylate.

11. An open cell porous polymeric material having a high internal phase emulsion stabilizing surfactant chemically bound to the polymeric material and a liquid capacity of from 70 to about 99 percent of its saturated state volume and prepared by polymerizing a water-in-oil high internal phase emulsion having an internal aqueous phase of greater than 70 percent by volume and an external oil phase comprising vinyl polymerizable monomers and a high internal phase emulsion stabilizing surfactant of which at least 50 weight percent chemically binds to the monomers that are polymerized.

12. The porous polymeric material of claim 11, wherein the surfactant is a surfactant having polymerizable vinyl groups.

13. The porous polymeric material of claim 12, wherein the surfactant having polymerizable vinyl groups is a substituted and/or conjugated alkene having hydrophilic and hydrophobic moieties which render the surfactant capable of forming a water-in-oil emulsion.

14. The porous polymeric material of claim 12, wherein the surfactant having polymerizable vinyl groups is a quaternary ammonium compound or a nonionic polymeric compound.

15. The porous polymeric material of claim 14 wherein the quaternary ammonium compound is N,N-dimethyl, N-erucyl, N-vinylbenzyl ammonium chloride or oleyl-hydroxyethyl-vinylbenzyl imidazolinium chloride.

16. An open cell porous polymeric material having a high internal phase emulsion stabilizing surfactant chemically bound to the polymeric material and a liquid capacity of from 70 to about 99 percent of its saturated volume, the stabilizing surfactant being an acrylate- or methacrylate-capped poly(ethylene oxide) (EO)/polybutylene oxide (BO) diblock polymer or an acrylate- or methacrylate-capped BO/EO/BO triblock polymer.

17. A process for preparing a porous polymeric material which comprises polymerizing a water-in-oil high internal phase emulsion having an internal aqueous phase of greater than 70 percent by volume and an external oil phase comprising vinyl polymerizable monomers and a high internal phase emulsion stabilizing surfactant of which at least 50 weight percent chemically binds to the monomers that are polymerized.

18. The process of claim 17, wherein the surfactant is a surfactant having polymerizable vinyl groups.

19. The process of claim 18, wherein the surfactant having polymerizable vinyl groups is a substituted and/or conjugated alkene having hydrophilic and hydrophobic moieties which render the surfactant capable of forming a water-in-oil emulsion.

20. The process of claim 19, wherein the surfactant having polymerizable vinyl groups is a quaternary ammonium compound or a nonionic compound.

21. The process of claim 20, wherein the quaternary ammonium compound contains an alkyl group having more than 12 carbons.

22. The process of claim 21, wherein the quaternary ammonium compound is N,N-dimethyl, N-erucyl, N-vinylbenzyl ammonium chloride or oleyl-hydroxyethyl-vinylbenzyl imidazolinium chloride.

23. A water-in-oil high internal phase emulsion comprising at least 70 volume percent of an high internal aqueous phase and less than 30 volume percent of an external oil phase which comprises a vinyl polymerizable monomer and a high internal phase emulsion stabilizing surfactant which chemically binds to the vinyl polymerizable monomer and/or polymerizing monomers under polymerization conditions.

24. A process for preparing a porous polymeric material which comprises polymerizing a water-in-oil high internal phase emulsion comprising at least 70 volume percent of an internal aqueous phase and less than 30 volume percent of an external oil phase which comprises vinyl polymerizable monomers and a high internal phase emulsion stabilizing surfactant which will chemically bond to the vinyl polymerizable monomers and/or polymerizing monomers under polymerization conditions.

25. An article comprising a porous polymeric material formed from a polymerized water-in-oil high internal phase emulsion comprising at least 70 volume percent of an internal aqueous phase and less than 30 volume percent of an external oil phase which comprises a vinyl polymerizable monomer and a high internal phase emulsion stabilizing surfactant which chemically binds to the vinyl polymerizable monomer and/or the polymerizing monomers under polymerization conditions.

26. The article of claim 25 which is an absorbent article, an insulating article or an article for sound, noise or vibration control.

27. The emulsion of claim 2 wherein the surfactant having polymerizable vinyl groups is a nonionic compound.

28. The emulsion of claim 2 wherein the polymerizable vinyl group comprises an $\alpha,\beta$-unsaturated carbonyl group.

29. The emulsion of claim 2 wherein the polymerizable vinyl group comprises a substituted aryl group with $\alpha,\beta$-unsaturation.

30. The porous polymeric material of claim 13 wherein the surfactant having polymerizable vinyl groups is a nonionic compound.

31. The porous polymeric material of claim 13 wherein the polymerizable vinyl group comprises an $\alpha,\beta$-unsaturated carbonyl group.

32. The porous polymeric material of claim 13 wherein the polymerizable vinyl group comprises a substituted aryl group with $\alpha,\beta$-unsaturation.

33. The process of claim 19 wherein the surfactant having polymerizable vinyl groups is a nonionic compound.

34. The process of claim 19 wherein the polymerizable vinyl group comprises an $\alpha,\beta$-unsaturated carbonyl group.

35. The process of claim 19 wherein the polymerizable vinyl group comprises a substituted aryl group with $\alpha,\beta$-unsaturation.

36. The process of claim 35, wherein the nonionic compound is an acrylate- or methacrylate-capped poly(ethylene oxide) (EO)/polybutylene oxide (BO) diblock polymer or an acrylate- or methacrylate-capped BO/EO/BO triblock polymer.

37. The emulsion of claim 29, wherein the nonionic compound is an acrylate- or methacrylate-capped poly(ethylene oxide) (EO)/polybutylene oxide (BO) diblock polymer or an acrylate- or methacrylate-capped BO/EO/BO triblock polymer.

* * * * *

UNITED STATES PATENT AND TRADEMARK OFFICE
CERTIFICATE OF CORRECTION

| | |
|---|---|
| PATENT NO. | : 5,977,194 |
| DATED | : November 2, 1999 |
| INVENTOR(S) | : Steven W. Mork et al. |

It is certified that error appears in the above-identified patent and that said Letters Patent is hereby corrected as shown below:

<u>Title page,</u>
Item [56], References Cited, under OTHER PUBLICATIONS,
After the word "Nostrand" delete the word "Reinhold" and insert therefore
-- Reinhold --.
After the word "Anionic" delete the word "Caly" and insert therefore -- Clay --
After the phrase "Flexible Polyurethane Foams", delete the word "Palstic" and insert therefore -- Plastic --.
After the word "Preparing" delete the word "Teh" and insert therefore -- The --.

U.S. PATENT DOCUMENTS,
Delete "Desmarais" and insert therefore -- DesMarais --.
At reference numbers 5,692,939, 5,741,581, and 5,763,499 delete "et al."

<u>Column 10,</u>
Lines 44 and 45, delete the phrase "Or a nonionic compound".

<u>Column 11,</u>
Line 8, delete the phrase "Or a nonionic compound".
Line 17, delete the word "high".

<u>Column 12,</u>
Line 13, 16 and 19, delete the number "13" and insert therefore -- 12 --.
Lines 22, 24 and 26, delete the number "19" and insert therefore -- 18 --.
Line 29, delete the number "35" and insert therefore -- 33 --.
Line 34, delete the number "29" and insert therefore -- 27 --.

Signed and Sealed this

Twenty-fifth Day of June, 2002

*Attest:*

*Attesting Officer*

JAMES E. ROGAN
*Director of the United States Patent and Trademark Office*